Dec. 12, 1972 C. G. KLEHM Plant Pat. 3,269
PEONY PLANT
Filed Feb. 18, 1971
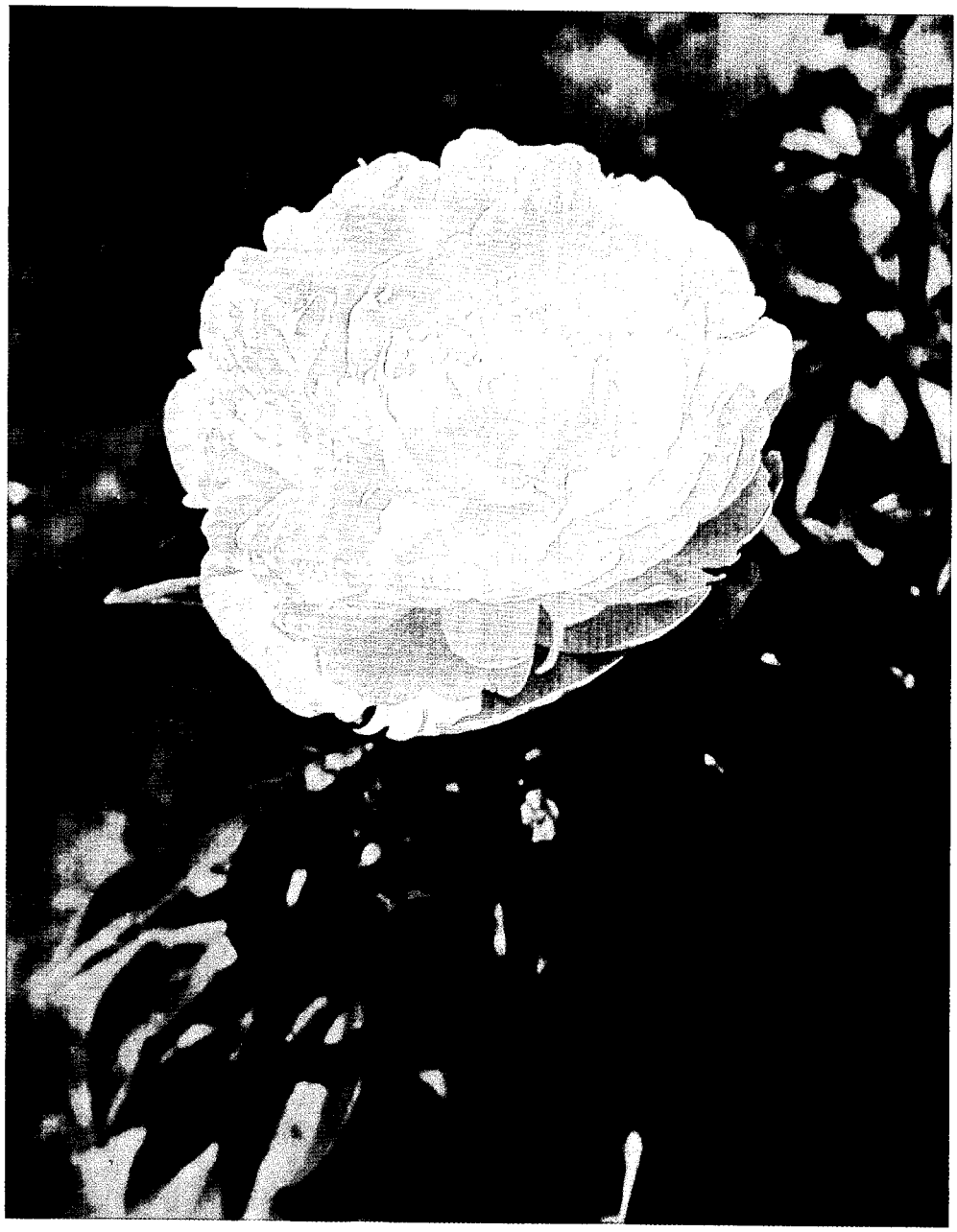
Inventor.
Carl G. Klehm
By: Robb & Robb
Attorneys.

United States Patent Office

Plant Pat. 3,269

Patented Dec. 12, 1972

3,269
PEONY PLANT

Carl G. Klehm, 2 E. Algonquin Road,
Arlington Heights, Ill. 60005

Filed Feb. 18, 1971, Ser. No. 116,688
Int. Cl. A01h 5/00
U.S. Cl. Plt.—68 1 Claim The present invention relates to a new and distinct variety of peony plant of the species botanically known as *Paeonia lactiflora,* which was originated by me by crossing two unnamed and unpatented line bred filial $F_1$ seedlings of the variety known as "Mons. Jules Elie" (unpatented), said seedlings being respectively identified in my breeding records as No. 69J and No. 69A, the former being the male parent and the latter being the female parent.

My new variety resulted from an extensive and prolonged program of breeding and testing conducted by me in an effort to produce new and improved or unique peony varieties, and was selected as one of many outstanding varieties resulting from this breeding program because of its unique combination of the following principal characteristics which distinguish the new variety from its parents, as well as from all other peony varieties of which I am aware:

(1) A short, petite and compact habit of growth, with a balanced and vigorous root system;

(2) Clean, disease free, lush green shoots, stems and foliage;

(3) A full-double, slightly flat rose type bloom form, with no stamens or carpels;

(4) A distinctive and attractive vivid coral pink flower color, with deeper highlights and a slight silver petal edging; and (5) Especial suitability for garden and landscape plantings, including neat and formal hedges, as well as groupings with other perennial settings.

Asexual reproduction of my new peony variety by root division, as performed by me in my nursery located at Arlington Heights, Ill., shows that the foregoing characteristics and distinctions come true to form and are established and transmitted through succeeding propagations.

The accompanying drawing shows typical specimens of the vegetative growth and flowers of my new variety, as depicted in color as nearly true as it is reasonably possible to make the same in a color illustration of this character.

The following is a detailed description of the new variety, with color terminology in accordance with the Horticultural Colour Chart (1966 Edition), published by The Royal Horticultural Society, of London, England, as based on specimens grown and observed by me at Arlington Heights and Barrington, Ill.

Breeding: Seedling.
- *Seed parent.*—An unnamed $F_1$ seedling identified as No. 69A.
- *Pollen parent.*—An unnamed $F_1$ filial seedling identified as No. 69J.

Propagation: Holds its distinguishing characteristics through succeeding propagations by root division.

*Flower*

Blooming habit: Annual.
Blooming season: Mid to mid-late season.
Bud:
- *Size.*—Medium large.
- *Form.*—Smooth; round.
- *Color.*—Neyron rose, Fan 1, Plate 55 B′.

- *Sepals.*—Even; smooth edge. Color—Green.
- *Opening.*—Opens easily and dependably; no splitting.

Bloom:
- *Size.*—Medium.
- *Borne.*—Singly; one main bud per stem, with from 0 to 3 auxiliary buds.
- *Stems.*—Short (from 20 inches to 23 inches); medium strong.
- *Form.*—Rose-type.
- *Petalage.*—Double.
- *Color.*—Vivid coral pink or Neyron rose, Fan 1, Plate 55 C′, with deeper highlights and a slight silver petal edging.
- *Variegations.*—None.
- *Discolorations.*—None.

Petals:
- *Texture.*—Medium thick.
- *Appearance.*—Shiny; neat.
- *Form.*—Smooth.
- *Arrangement.*—Imbricated.
- *Persistence.*—Average.
- *Fragrance.*—Slight.
- *Lasting quality.*—Average.

*Reproductive organs*

None: completely petaloid.
Fruit: None.

*Plant*

Form: Short bush.
Growth: Healthy; vigorous.
Foliage:
- *Leaflets.*—4 in number.
- *Size.*—Medium.
- *Quantity.*—Medium.
- *Color.*—Lush bottle green, Fan 3, Plant 135 B′.
- *Shape.*—Elliptically acute.
- *Texture.*—Gloosy; smooth.
- *Edge.*—Smooth.
- *Serrations.*—None.
- *Leaf stem.*—Medium thick.
- *Stipules.*—None
- *Disease resistance.*—Resistant to leaf blotch and other bacterial peony diseases as determined by comparison with other varieties for many years as grown at Arlington Heights and Barrington, Ill.

*General observations*

The new variety is considered as being distinctively unique primarily because of its short habit of growth and its outstanding vivid flower color.

I claim:

1. A new and distinct variety of peony plant of the species botanically known as *Paeonia lactiflora,* substantially as herein shown and described, characterized particularly as to novelty by the unique combination of a short, petite and compact habit of growth, with a balanced and vigorous root system, clean, disease free, lush green shoots, stems and foliage, a full-double, slightly flat rose type bloom form, with no stamens or carpels, a distinctive and attractive vivid coral pink flower color, with deeper highlights and a slight silver petal edging, and especial suitability for garden and landscape plantings, including neat and formal hedges, as well as groupings with other perennial settings.

No references cited.

ROBERT E. BAGWILL, Primary Examiner